United States Patent [19]

Flaum

[11] 4,384,205
[45] May 17, 1983

[54] NEUTRON METHOD AND APPARATUS FOR DETERMINING TOTAL CROSS-SECTION

[75] Inventor: Charles Flaum, Danbury, Conn.

[73] Assignee: Schlumberger Technology Corporation, New York, N.Y.

[21] Appl. No.: 204,094

[22] Filed: Nov. 5, 1980

[51] Int. Cl.³ .............................................. G01V 5/00
[52] U.S. Cl. .................................... 250/265; 250/269
[58] Field of Search ............... 250/270, 269, 262, 264, 250/265, 266

[56] References Cited

U.S. PATENT DOCUMENTS

| | | |
|---|---|---|
| 2,667,583 | 1/1954 | Herzog . |
| 2,971,094 | 2/1961 | Tittle . |
| 3,435,217 | 3/1969 | Givens . |
| 3,483,376 | 12/1969 | Locke et al. . |
| 3,566,116 | 2/1971 | Nelligan . |
| 3,691,378 | 9/1972 | Hopkinson et al. . |
| 4,004,147 | 1/1977 | Allan .................................. 250/264 |
| 4,005,290 | 1/1977 | Allan .................................. 250/266 |
| 4,021,666 | 5/1977 | Allan .................................. 250/265 |
| 4,095,102 | 6/1978 | Tixier ................................. 250/265 |
| 4,251,724 | 2/1981 | Vagelatos et al. ................. 250/264 |

Primary Examiner—Alfred E. Smith
Assistant Examiner—Carolyn E. Fields
Attorney, Agent, or Firm—Stephen L. Borst

[57] ABSTRACT

A method and an apparatus for quantitatively determining the macroscopic thermal neutron absorption cross-section of a geological formation traversed by a borehole is disclosed. The method comprises the steps of irradiating the formation with neutrons from a continuous source in a neutron sonde and detecting through the use of dual epithermal and thermal detectors the resultant flux of both thermal and epithermal neutrons. Representative signals are then combined in a manner which best takes advantage of the physics of the interaction of neutrons with matter to produce a representation of the macroscopic thermal neutron absorption cross-section. Thus, a signal representing the ratio of the counts is derived from each like pair of detectors. The logarithms of the signals are then taken and combined in a linear combination.

20 Claims, 3 Drawing Figures

NEUTRON METHOD AND APPARATUS FOR DETERMINING TOTAL CROSS-SECTION

TECHNICAL FIELD OF THE INVENTION

The present invention relates generally to the field of material analysis and the determination of the characteristic properties of the material. More specifically, the invention relates to a nuclear method and apparatus for determining the macroscopic neutron absorption cross-section of a material. More particularly yet, the present invention relates to the determination of the macroscopic neutron absorption cross-section of the materials comprising the geological formation surrounding a bore hole.

BACKGROUND OF THE INVENTION

It is well known in the field of oil well analysis, that reliable determination of the macroscopic neutron absorption cross-section (frequently referred to as Sigma) of the materials surrounding a borehole penetrating a geological formation can be of great assistance in well evaluation. For example, since the formation fluids are normally either salt water (having a relatively high Sigma) or hydrocarbons (having a smaller SIGMA), knowledge of Sigma enables the recognition of oil versus water in the formation. The same differences in Sigma may be used to help in the identification of the oil/water interface in the formation. Additionally, if two logs of Sigma are taken at different times, the production of the hydrocarbon bearing formation may be monitored. Permeable zones of a hydrocarbon bearing formation may be distinguished from less permeable zones by examination of the log of Sigma since the more permeable zones will be invaded by the mud filtrate (usually saline water having a Sigma much greater than that of the displaced hydrocarbon). And finally, Sigma is frequently used as a shale indicator. As a result of these many uses of Sigma, a variety of techniques have been developed to enable determination of this important formation characteristic.

For example, U.S. Pat. Nos. 3,566,116; 3,691,378; and 4,055,763 illustrate variations of one such technique in which a pulsed neutron source is utilized to repetitively irradiate the formation with a burst of fast neutrons in order to permit a time evaluation of the neutron population in the resultant neutron cloud. Typically, this evaluation is accomplished by detecting capture gamma rays which result when thermalized neutrons of the cloud are captured or absorbed by a nucleus of a constituent element in the formation. In such a time evaluation, advantage is taken of the fact that the neutron cloud density decays exponentially, with the characteristic decay time being a function of the macroscopic neutron absorption cross-section of the formation. The macroscopic neutron absorption cross-section is the sum of the neutron absorption of the elemental constituents of the formation and of its contained fluids.

One limitation that the pulsed neutron techniques for determining Sigma have encountered is their inability to properly determine Sigma in a formation containing large amounts of naturally radioactive elements such as thorium, uranium and potassium. Accumulations of one or more of these radioactive elements may produce a gamma ray background that obscures the desired information relative to the neutron cloud established by the pulsed neutron source. Unfortunately, accumulations of naturally occuring radioactive elements are often encountered in a producing well. It has been found that radioactive particulates which may be found in formation fluids tend to be filtered out and accumulate at the well casing perforations through which the formation fluids are flowed to create a naturally radioactive accumulation that decays to produce a relatively high gamma ray background which interferes with the detection method of the pulsed neutron technique. Thus, information regarding Sigma and oil/water movements in the very formation zones of greatest interest may be unavailable due to this obscuring background.

An additional limitation with the pulsed neutron technique is encountered in wells that have fresh water in the well borehole. In such a circumstance, some neutrons from the pulse are thermalized and linger in the fresh water of the borehole, giving rise to an interfering "diffusion" background. This effect of course does not occur in those boreholes having saline water since the chlorine is a strong neutron absorber and rapidly scavenges the diffusion neutrons. The "diffusion" background is a particularly bothersome phenomenon for the pulsed neutron technique since the determination of the characteristic decay time following the neutron burst relies on the detection of neutron fluxes whose intensities decrease with time to relatively small values. As a result, the "diffusion" background becomes large relative to the neutron flux of interest so as to obscure the information bearing signal.

In addition to those techniques which make a time analysis following a neutron burst, at least one other technique for the determination of the macroscopic neutron absorption cross-section has been attempted. This technique utilizes a continuous neutron source to irradiate the formation with a relatively high flux of relatively high energy neutrons. The spatial distribution of the resultant neutron cloud is concurrently examined by a pair of radiation detectors spaced from the source. One of the detectors responds to the presence of thermal neutrons while the other is responsive to the presence of epithermal neutrons. Advantage is then made of the fact that the spatial distribution of the epithermal neutrons is functionally related to the porosity of the formation while the spatial distribution of the thermal neutrons is functionally related both to the porosity of the formation and to the macroscopic neutron absorption cross-section of the formation.

A first example of a technique which has attempted to take advantage of this fact is the technique disclosed in U.S. Pat. No. 2,667,583. There it was proposed to detect the interface between a brine native to earth formations and liquid hydrocarbon by subjecting the earth formation to a fast neutron flux, and to produce two electrical signals dependent repectively upon the detection of neutrons having thermal and greater energies (thermal neutrons and epithermal neutrons), and the detection of neutrons having greater than thermal energies (eptithermal neutrons). It was suggested in that patent that the resultant signals be subtracted one from another with their difference being indicative of a qualitative indication of the presence of salt water or hydrocarbon containing formations.

U.S. Pat. No. 2,971,094 suggests a closely related although improved technique in which a first detector is sensitive substantially solely to neutrons having epithermal energies, while a second detector is sensitive substantially solely to thermal neutrons. In the practice of the disclosed invention there, the signals from the detectors may be either subtracted to form a difference or divided to form a ratio. Further, it is suggested in that patent that a strong thermal neutron absorber be artificially introduced into the earth formations by incorporating a strong thermal neutron absorber in the drilling fluid in order to produce an overall increase in the thermal neutron absorbing characteristics of the earth formation.

As a further example of a prior art technique which utilizes a continuous source of neutrons to bombard the formation, U.S. Pat. No. 3,435,217 proposes that a first detector record thermal neutrons, that a second detector record epithermal neutrons and that a third detector record capture gamma rays. In that patent, it is taught that the epithermal neutron signal is dependent upon the porosity but independent of the chemistry of the formation, while both the thermal neutron and the capture gamma ray signals are dependent upon the chemistry of the formation as well as the porosity of the formation. These signal dependencies are used to advantage to remove the porosity dependence of the thermal neutron and capture gamma ray signals by their appropriate combination with the epithermal neutron signal. In making this combination, a graphical technique is utilized for converting the epithermal signal into a porosity component of the thermal neutron signal and a porosity component of the gamma ray signal. These porosity components are then removed from the thermal neutron signal and from the gamma ray signal, respectively, by taking the appropriate ratios. Finally, the resultant chemistry dependent but porosity independent thermal neutron and gamma ray signals are referenced to shale.

Finally, U.S. Pat. No. 4,005,290 discloses a technique in which the ratio formed from a pair of epithermal neutron detectors is compared with the ratio of the signals derived from a pair of thermal neutron detectors in order to determine a differential therebetween, said differential yielding a qualitative indication of the salinity of the formation.

While each of the above techniques is free of the mentioned limitation of the previously described timing technique, since they detect neutrons as opposed to gamma rays and are therefore not influenced by gamma ray backgrounds, and since the neutron flux of interest is large compared to the "diffusion" background so that the "diffusion" neutron flux from fresh water filled boreholes is not a serious difficulty, they have not been well received in the commercial world primarily due to their unfortunate inability to provide satisfactory quantitative values of Sigma as opposed to general qualitative values. This inability stems from the lack of a complete understanding of the physics inherent in the spatial distribution of thermal and epithermal neutrons relative to the location of the irradiating neutron space. It is evident that recognition of the proper functional relationship between the spatial distribution of the thermal and epithermal neutrons and the Sigma of the formation is necessary before such techniques can be made to yield quantitative as opposed to qualitative determinations of Sigma.

SUMMARY OF THE INVENTION

The present invention cures the deficiencies of the prior art continuous neutron source techniques by providing a continuous neutron source apparatus and method for quantiatively determining the macroscopic neutron absorption cross-section of an examined material. In accordance with the principles of the invention, it has been recognized that the logarithmic nature of the spatial distribution of the neutron cloud may be applied in a manner to determine a quantitative indication of Sigma rather than merely a qualitative one. Accordingly, both thermal and epithermal count rate signals are derived from the neutron irradiated material. These count rate signals, which are representations of the spatial distribution of neutrons in the material resulting from the irradiation of the material with a continuous neutron source, are then combined in a manner which yields a quantitative determination of macroscopic neutron absorption cross-section. Specifically, the logarithms of the thermal and epithermal signals are combined in a linear combination to give a value for macroscopic neutron absorption cross-section. The coefficients of the linear combination are dependent on the characteristics of the apparatus used in the investigation.

In one embodiment of the invention, a geological formation penetrated by a borehole is logged with a nuclear logging tool containing a continuous neutron source, a single thermal neutron detector spaced therefrom, and a single epithermal neutron detector also spaced therefrom. Count rate signals are derived from each of these detectors. The count rate signals are then modified by taking their logarithms. The logarithm signals are further modified by constant multiplicative calibration values determined for the particular tool used in the logging operation. Finally, the modified logarithmic count rate signals are combined with one another in a linear combination which yields an improved signal quantitatively indicative of the macroscopic neutron absorption cross-section of the geological formation under investigation. Specifically, the modified logarithmic thermal count rate signal is subtracted from the modified logarithmic epithermal count rate signal and their difference is added to a calibration constant.

In a second embodiment of the invention, the geological formation is logged with a nuclear tool containing a continuous neutron source and a pair of differently spaced thermal neutron detectors as well as a pair of differently spaced epithermal neutron detectors. Count rate signals are derived from each of these detectors. Count rate signal ratios are next formed from the thermal detector signals as well as from the epithermal detector signals. The count rate ratio signals are then modified by taking their logarithms respectively. The logarithmic ratio signals are further modified by constant multiplicative calibration values determined for the particular tool used in the logging operation. Finally, the modified thermal and epithermal logarithmic count rate ratio signals are combined with one another in a linear combination which yields an improved signal quantitatively indicative of the Sigma of the formation. In this embodiment, the modified epithermal and thermal logarithmic count rate ratio signals are added to one another, and their sum is subtracted from a tool dependent calibration constant.

BRIEF DESCRIPTION OF THE DRAWINGS

The present invention may be better understood and its numerous objects and advantages will become apparent to those skilled in the art by reference to the accompanying drawings wherein like reference numerals refer to like elements in the several figures and in which.

BRIEF DESCRIPTION OF THE INVENTION

While the invention is susceptible of various modifications and alternative constructions, there is shown in the drawings and there will hereinafter be described, in detail, a description of the preferred or best known mode of the invention. It is to be understood, however, that the specific description and drawings are not intended to limit the invention to the specific form disclosed. On the contrary, it is intended that the scope of this patent include all modifications and alternative constructions thereof falling within the spirit and scope of the invention as expressed in the appended claims, to the full range of their equivalents.

As has been previously described, a number of prior art techniques have been developed to determine macroscopic neutron absorption cross-section. At least one of these techniques involves irradiating the material under investigation with a time-wise continuous source of high energy neutrons and detecting, at locations spaced from the source, both thermalized neutrons and epithermal neutrons. Signals indicative of each of the respective neutron fluxes, usually in the form of count rate signals, are then combined in an attempt to determine macroscopic neutron absorption cross-section by utilizing the knowledge that the magnitude of the epithermal neutron signal is functionaly related to the Hydrogen Index of the material under investigation which in turn is closely related to fluid filled porosity, while the magnitude of the thermal neutron signal is functionally related to both the Hydrogen Index and the macroscopic thermal neutron capture cross-section of the material, (Sigma). These previous attempts have achieved a limited success by demonstrating a qualitative Sigma response but have failed in producing a quantitative Sigma response.

The present invention overcomes the inadequacy of the prior art and produces a repeatable, quantitative indication of Sigma by applying a more complete understanding of the physics of neutron interaction with matter. Specifically, it has been recognized that the flux of epithermal neutrons passing through and interacting with matter is governed by their mean free path, which is inversely proportional to interaction cross section. The radial distribution of the epithermal neutron flux is a decreasing exponential function of the distance from the neutron source divided by the mean free path, $$FE = (a/R)e^{(-R/Le)} \quad (1)$$

where FE=epithermal neutron flux, R=source detector spacing, Le=epithermal neutron mean free path, and a is a proportionality constant.

Expressed in another way, the radial distribution of the epithermal neutron flux is an exponential function of the product of source detector distance and epithermal neutron scattering cross-section, since cross-section is proportional to the inverse of the path length. From this, it follows that the logarithm of the count rate is proportional to the epithermal neutron scattering cross-section.

$$\log (FE) = k_1 + K_1 \text{ Sigma (scattering)} \quad (2)$$

By a similar analysis, one can arrive at a similar relationship for Sigma (thermal or capture). Since the source is a high energy neutron source, the thermal neutron flux will depend not only on the capture cross-section of the thermal neutrons but also on the scattering cross-section of the intermediate epithermal neutrons. Thus $$\log (FT) = k_2 + K_2 [\text{Sigma (scattering)} + \text{Sigma (thermal or capture)}]. \quad (3)$$

Combining equations (2) and (3), we arrive at the equation $$\text{Sigma (thermal)} = A + B \log (FE) - C \log (FT) \quad (4)$$

where constants A, B, and C are tool dependent constants.

Figure 3:
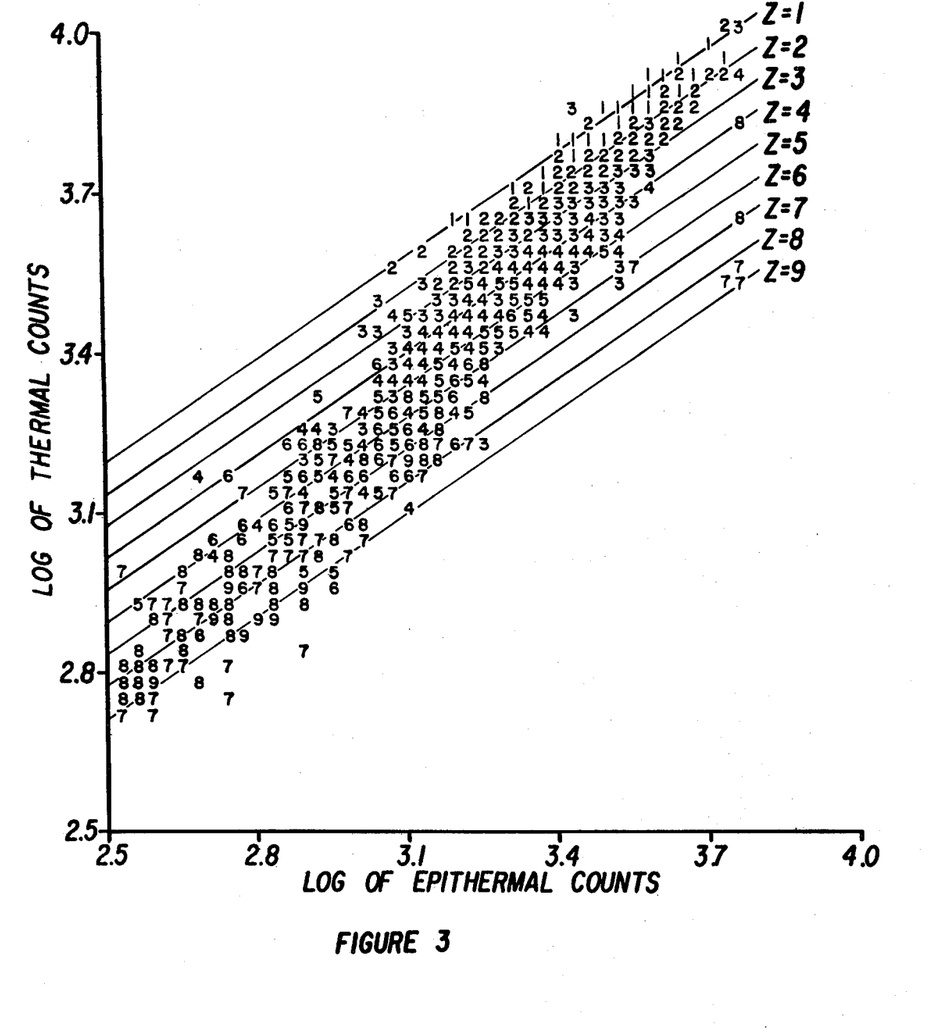
FIG. 3 is a histogram type cross-plot of the logarithm of thermal counts versus the logarithm of the epithermal counts which reveals the relationship between these quantities and macroscopic neutron absorption cross-section.

FIG. 3 is a cross-plot of the logarithm of thermal count rate on the Y-axis versus the logarithm of the epithermal count rate on the X-axis. In the special presentation of FIG. 3, each data point on the crossplot has been associated with a value of Sigma determined by means independent of the technique of the present invention. This has been done by assigning to each data point one of nine families designated by an integer value from 1 to 9 as determined by the relationship Sigma = 10 + 2.29Z where $$Z = 1, \ldots 9.$$

This technique is actually a method of plotting data in two dimensions in a manner which shows a three-dimensional dependency (i.e., x, y nd z corresponding to epithermal counts, thermal counts and thermal neutron capture cross-section (Sigma)).

From an examination of FIG. 3, one may immediately note (with the aid of the plurality of parallel, equally spaced straight lines passing generally through the locus of each Sigma family) that the Sigma families are separated from one another and that the Sigma families are each functions of the logarithm of the thermal counts as well as of the logarithm of the epithermal counts. It will be recognized that this behavior confirms the previously postulated relationship $$\text{Sigma (thermal)} = A + B \log (FE) - C \log (FT) \quad (5)$$

It should be recognized that there are additional variables that may have an effect on the results discussed above and may or may not have to be taken into consideration. In a well logging tool, an example of such an additional variable is the effect of borehole washout and standoff of the tool from the formation. In an optimized embodiment, standoff will tend to effect the epithermal count rate or flux to a somewhat larger degree than the thermal count rate or flux, thereby causing data points to shift, parallel to a particular Sigma family, resulting in a small effect on the value of Sigma.

A similar analysis can be made for a tool that has a pair of differently spaced epithermal and a pair of differently spaced thermal detectors whose signals are combined to produce epithermal and thermal ratios instead of simple single detector count rates. This approach has the advantage of permitting the use of explicit environmental corrections. Additionally, since ratios are self calibrating, tool-to-tool variations may be easily eliminated. The governing relationship for count rate ratios is as follows.

$$\text{Sigma (thermal)} = A - B \log (RE) + C \log (RT)$$

where RE and RT are the epithermal and thermal count rate ratios respectively.

Figure 1:
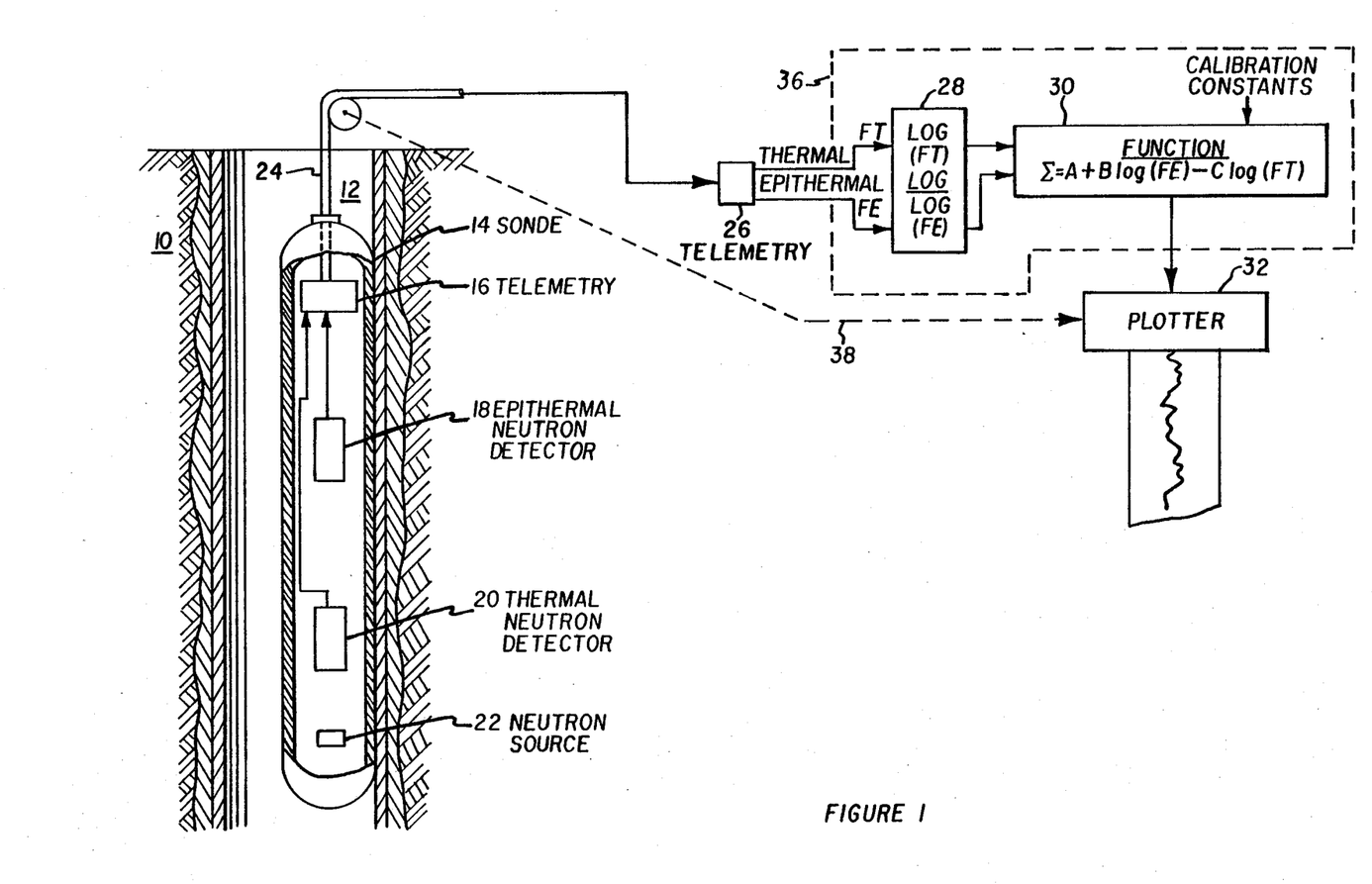
FIG. 1 is a schematic rendition of one mode of practicing the invention.

Turning now to FIG. 1, a first embodiment of the invention will be described in the context and environment of a process and apparatus for logging a geological formation 10 traversed by a borehole 12. The logging apparatus or sonde 14 comprises a pressure housing enclosing a neutron source 22, an epithermal neutron detector 18, and a thermal neutron detector 20, both spaced from the neutron source by a predetermined distance. Neutron source 22 may, for example, comprise an AmBe continuous chemical source, but it will be understood by those skilled in the art that the invention is not limited to the use of such a continuous neutron source and may be practiced with a pulsed neutron source of suitable intensity. Neutron detectors 18 and 20 are preferably of the $He^3$ type. There are gas filled counting tubes filled with $He^3$ gas under pressure. The $He^3$ detectors respond to neutrons scattered back to the detectors from the surrounding earth formations. As will be appreciated, epithermal neutron detector 18 preferably includes an external cadmium sleeve which prevents thermal neutrons from gaining access to the $He^3$ detector. The higher energy epithermal neutrons penetrate the cadmium sleeve more readily so that their detection is assured. It may be found to be desirable to provide the epithermal detector with a higher $He^3$ pressure than that of the thermal detector. Otherwise, the designs of detectors 18 and 20 are well known and are not an aspect of the present invention so that further description will be omitted for the sake of brevity.

Voltage pulses from the neutron detectors 20 and 22 are amplified by amplifiers (not shown), temporarily stored in buffers (also not shown), and subsequently delivered to the surface through appropriate telemetry circuitry 16 through the wireline 24 from which the sonde 14 is suspended. At the surface, the telemetered data is received by suitable telemetry circuitry 26 and sorted into thermal and epithermal count rate signals. Telemetry circuits 16 and 26 are standard units and are well within the knowledge of persons ordinarily skilled in the logging art so that their detailed description is also omitted in the interest of conciseness.

The thermal and epithermal count rate signals are delivered from surface telemetry circuit 26 to a logging computer 36 for further processing. Logging computer 36 may comprise a network of suitable analog components or, more preferably, logging computer 36 may comprise a special or a suitably programmed general purpose digital computer such as the PDP 11/47 computer manufactured by the Digital Equipment Corporation, Maynard, Massachusetts. Be that as it may, the basic operations accomplished by the logging computer 36, be it an analog computer or a digital computer, are represented by elements 28 and 30 of FIG. 1. Element 28, labeled "log" as an abbreviation for logarithm, takes the logarithm of both the thermal count rate signal and the epithermal count rate signal. The count rate logarithm signals are then combined in element 30, labeled "function", according to the linear equation:

$$\text{Sigma} = A + B \log (FE) - C \log (FT)$$

In this relationship, constants A, B and C are tool dependent calibration constants which assume different values for the different tools. For example, the values of constants A, B and C are dependent upon such tool characteristics as source intensity, source-detector spacing, and sensor sensitivity or efficiency. Once Sigma has been determined by element 30, an output signal is generated and delivered to a recording device such as that shown in the figure as plotter 32 which produces a continuous record of values of Sigma according to depth of the sonde in the borehole in response to a depth signal delivered via line 38, as is well known in the art.

Figure 2:
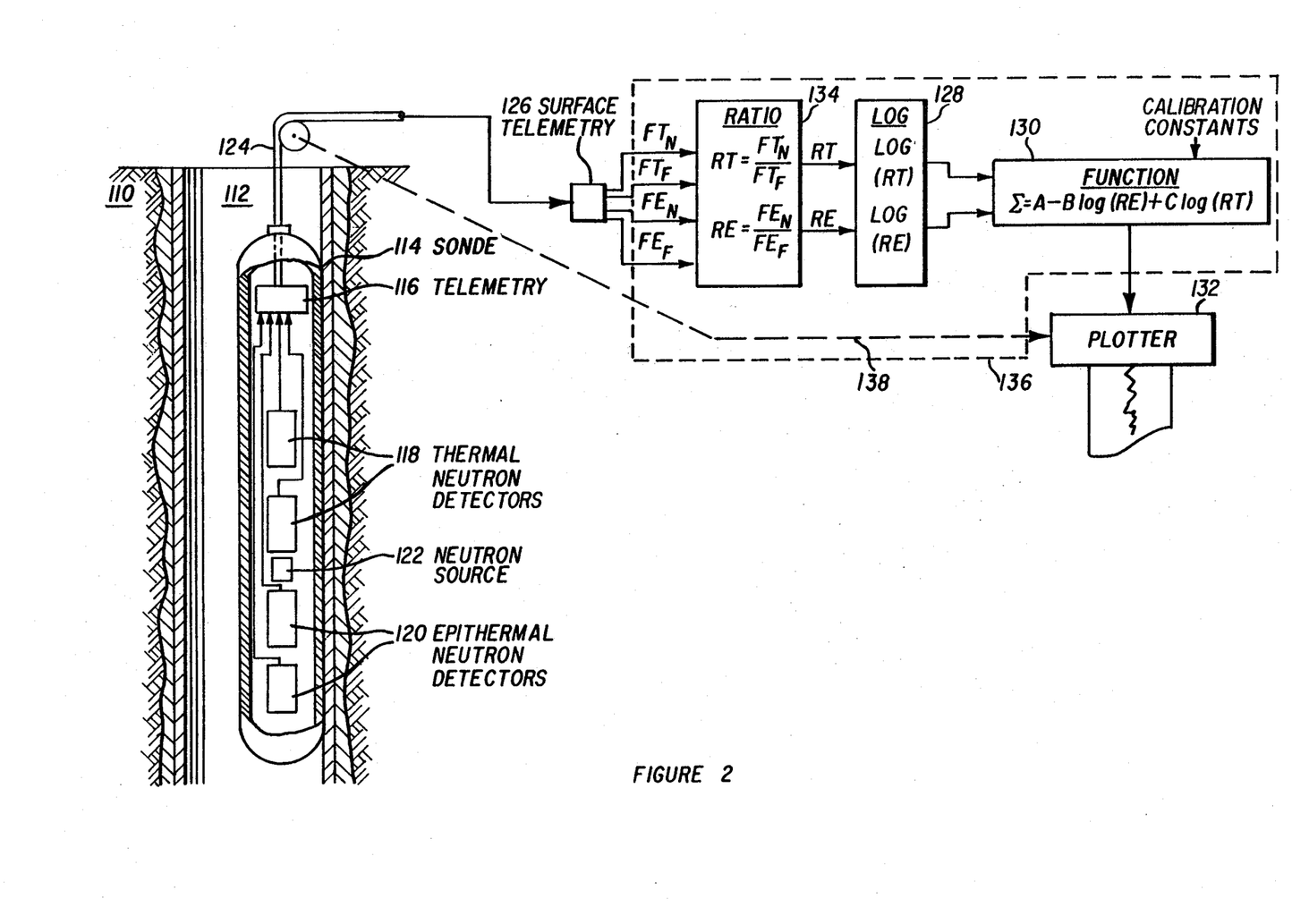
FIG. 2 is a schematic rendition of another mode of practicing the invention.

Turning now to an examination of FIG. 2, a second embodiment will be described. In a manner very similar to that described in the embodiment of FIG. 1, a sonde 114 is moved through a borehole 112 in a formation 110. Sonde 114 in this embodiment includes a neutron source 122, a pair of thermal neutron detectors 118, and a pair of epithermal neutron detectors 120. The thermal neutron detectors 118 are spaced along the length of the tool so that each member of the pair is spaced from the neutron source 122 by a different distance. Accordingly, one of the thermal neutron detectors is designated the near detector and the other detector is designated the far detector. The epithermal neutron detectors 120 are also positioned at different distances from the neutron source 122 so that one is designated the "near detector" and the other is designated the "far detector". Signals from all four of the detectors in the sonde are collected in the telemetry unit 116 and are subsequently delivered uphole via cable 124 to the surface telemetry unit 126 where they are unscrambled, separated and transferred to the logging computer 136. In this embodiment, logging computer 136 consists of a "ratio" element 134, a "log" element 128, and a "function" element 130. Ratio element 134 forms a ratio (RT) from the thermal count rate of the near detector amd the thermal count rate of the far detector as well as a ratio (RE) from the count rate of the near epithermal detector and the count rate from the far epithermal detector. Element 128 then takes the logarithm of the (RT) signal and the logarithm of the (RE) signal before function element 130 combines the logarithm signals in a linear combination according to the relationship $$\text{Sigma} = A - B \log (RE) + C \log (RT).$$

The Sigma output of element 130 is recorded on plotter 132 in response to the depth of the sonde 114 in the boreholes according to a depth signal delivered via line 138. In a manner similar to that already described, constants A, B and C are now calibration constants having different values which are predetermined for the particular circumstances of the well logging operation. This second embodiment, in which the thermal and epithermal count rate ratios are determined and used, has the advantage that the count rate ratios are normally calibrated so as to eliminate the tool-to-tool variations due to source strength and detector sensitivity. Accordingly, calibration constants A, B and C are design constants.

The present invention may find a particularly suitable application in a technique for monitoring the production of a hydrocarbon producing well. In the histroy of a well, the borehole is first drilled down to and through the formation to be produced, and then is typically logged with a variety of logging tools that yield a variety of information. One of the common tools that is used in the open-hole environment (i.e. before casing is run into the borehole and set with cement), is the compensated neutron tool: versions of which have been illustrated in FIGS. 1 and 2 and which have been described above. Heretofore, the compensated neutron tool has been used as a tool for investigating the porosity of the formation. With the invention herein disclosed, the compensated neutron tool may also find utility as a device and technique for forming an initial record or "log" of the macroscopic thermal neutron absorption cross-section. This "log" then provides a base record of macroscopic thermal neutron absorption cross-section which may be referenced against by comparing it to "logs" of macroscopic thermal neutron absorption cross-section obtained subsequent to the running and setting of casing and/or subsequent to well production. These "before" and "after" logs will show differences indicative of the change of the fluids in the formation adjacent to the borehole. Additionally, the "before" log of Sigma may be useful as a different type of shale indicator or as an indicator of water saturation in non drilling-mud invaded zones. Finally, the "before" Sigma log may be used in a calibration procedure to determine the shift in Sigma that may result with the installation of the casing and cement.

During the drilling operation, mud filtrate invades the formation: to a greater degree in permeable zones and to a lesser degree in less permeable zones. The "base" log may therefore be compared to a log of Sigma obtained after the casing has been set to get some measure of the permeability of the formation since the mud filtrate usually disperses and is replaced by bona fide formation fluids shortly after the casing has been set. In the event that the formation fluids are hydrocarbons, the resultant difference in Sigma due to the return of the hydrocarbon and the dispersal of the drilling mud filtrate will be quite apparent.

I claim:

1. A method for quantitatively determining the macroscopic neutron absorption cross-section of a geological formation traversed by a borehole, wherein said method comprises the steps of:
   a. passing a logging sonde through said borehole while continuously irradiating said formation with a continuous source of neutrons;
   b. detecting an epithermal neutron flux with a first detector carried by said sonde and spaced from said source of neutrons;
   c. detecting a thermal neutron flux with a second detector carried by said sonde also spaced from said source of neutrons;
   d. generating electrical signals indicative of said detected epithermal neutron flux and of said thermal neutron flux; and
   e. combining said electrical signals indicative of said detected epithermal neutron flux and of said thermal neutron flux to generate a signal representative of the macroscopic neutron absorption cross-section of said geological formation according to the relationship:

$$SIGMA = A + B \log (FE) - C \log (FT)$$

where SIGMA is the macroscopic neutron absorption cross-section of said material, (FE) is the signal indicative of epithermal neutrons, (FT) is the signal indicative of thermal neutrons, and A, B, and C are constants.

2. A method for quantitatively determining the macroscopic neutron absorption cross-section of a geological formation traversed by a borehole, wherein said method comprises the steps of:
   a. passing a logging sonde through said borehole while continuously irradiating said formation with a continuous source of neutrons;
   b. detecting an epithermal neutron flux at each one of a first pair of detectors carried by said sonde and spaced different distances from said source of neutrons;
   c. detecting a thermal neutron flux at each one of a second pair of detectors carried by said sonde and spaced different distances from said source of neutrons;
   d. generating a first electrical signal indicative of the spatial distribution of epithermal neutrons;
   e. generating a second electrical signal indicative of the spatial distribution of thermal neutrons;
   f. combining said first and second electrical signals to generate a signal representative of the macroscopic neutron absorption cross-section of said geological formation.

3. The method as recited in claim 2 wherein said first electrical signal is indicative of the ratio of counts from said first pair of detectors and wherein said second electrical signal is indicative of the ratio of counts from said second pair of detectors and wherein said combining step is performed according to the relationship:

$$SIGMA = A - B \log (RE) + C \log (RT)$$

where SIGMA is the macroscopic neutron absorption cross-section of said material, (RE) is the signal indicative of the ratio of epithermal neutron counts, (RT) is the signal indicative of the ratio of thermal neutron counts, and A, B, and C are constants.

4. A method for quantitatively determining the macroscopic neutron absorption cross-section of a material irradiated by a continuous neutron source, wherein said method comprises the steps of:
   a. deriving a first signal indicative of thermal neutrons emanating from said material;
   b. deriving a second signal indicative of epithermal neutrons emanating from said material;
   c. taking the logarithm of said first and second signals to generate first and second logarithm signals respectively; and
   d. combining said first and second logarithm signals in a linear combination to generate a signal representative of the macroscopic neutron absorption cross-section of the material.

5. The method as recited in claim 4 wherein said deriving steps include using a single detector for detecting thermal neutrons and a single detector for detecting epithermal neutrons.

6. The method as recited in claim 4 wherein said deriving steps include using a pair of spaced detectors for detecting thermal neutrons and a pair of spaced detectors for detecting epithermal neutrons in order to derive first and second electrical signals indicative of the spatial distribution of thermal and epithermal neutrons respectively.

7. The method as recited in claim 6 wherein said first electrical signal is indicative of the ratio of counts from said first pair of detectors and wherein said second electrical signal is indicative of the ratio of counts from said second pair of detectors and wherein said combining step is performed according to the relationship:

SIGMA = A − B log (RE) + C log (RT)

where SIGMA is the macroscopic neutron absorption cross-section of said material, (RE) is the signal indicative of the ratio of epithermal neutron counts, (RT) is the signal indicative of the ratio of thermal neutron counts, and A, B and C are constants.

8. A method for quantitatively determining the macroscopic neutron absorption cross-section of a material, wherein said method comprises the steps of:
   a. irradiating the material with neutrons from a continuous source;
   b. monitoring radiation emanating from the material to generate a first signal indicative of thermal neutrons;
   c. monitoring radiation emanating from the material to generate a second signal indicative of epithermal neutrons;
   d. taking the logarithm of said first and second signals to generate first and second logarithm signals respectively; and
   e. combining said first and second logarithm signals in a linear combination to generate a signal representative of the macroscopic neutron absorption cross-section of said material.

9. The method as recited in claim 4 or 8 wherein said combining step is performed in accordance with the following relationship:

SIGMA = A + B log (FE) − C log (FT)

where SIGMA is the macroscopic neutron absorption cross-section of said material, (FE) is the signal indicative of epithermal neutron flux, (FT) is the signal indicative of thermal neutron flux, and A, B, and C are calibration constants.

10. The method as recited in claim 4 or 8 wherein the material comprises a geological formation traversed by a borehole.

11. The method as recited in claim 4 or 8 wherein said first and second signals indicative of thermal and epithermal neutrons respectively are representative of the spatial distribution of neutrons.

12. The method as recited in claim 8 wherein said monitoring steps include using a single detector for detecting thermal neutrons and a single detector for detecting epithermal neutrons.

13. The method as recited in claim 8 wherein said monitoring steps include using a pair of spaced detectors for detecting thermal neutrons and a pair of spaced detectors for detecting epithermal neutrons in order to derive first and second electrical signals indicative of the spatial distribution of thermal and epithermal neutrons respectively.

14. The method as recited in claim 13 wherein said first electrical signal is indicative of the ratio of counts from said first pair of detectors and wherein said second electrical signal is indicative of the ratio of counts from said second pair of detectors and wherein said combining step is performed according to the relationship:

SIGMA = A − B log (RE) + C log (RT)

where SIGMA is the macroscopic neutron absorption cross-section of said material, RE is the signal indicative of the ratio of epithermal neutron counts, RT is the signal indicative of the ratio of thermal neutron counts, and A, B, and C are constants.

15. An apparatus for quantitatively determining the macroscopic neutron absorption cross-section of a neutron irradiated material, wherein said apparatus comprises:
   a. means for deriving a signal indicative of thermal neutrons;
   b. means for deriving a signal indicative of epithermal neutrons;
   c. means for taking the logarithms of said thermal and epithermal neutron signals; and
   d. means for combining said thermal and epithermal neutron logarithm signals to generate a signal representative of the macroscopic neutron absorption cross-section of the material.

16. An apparatus for quantitatively determining the macroscopic neutron absorption cross-section of a material, wherein said apparatus comprises:
   a. a neutron source for irradiating the material with neutrons;
   b. detector means for monitoring radiation emanating from the material to generate a signal indicative of thermal neutrons;
   c. detector means for monitoring radiation emanating from the material to generate a signal indicative of epithermal neutrons;
   d. means for taking the logarithms of said thermal and epithermal neutron signals; and
   e. means for combining the logarithms of said thermal and epithermal neutron signals to generate a signal representative of the macroscopic neutron absorption cross-section of said material.

17. An apparatus for quantitatively determining the macroscopic neutron absorption cross-section of a neutron irradiated material, wherein said apparatus comprises:
   a. first means for deriving a signal indicative of thermal neutrons;
   b. second means for deriving a signal indicative of thermal neutrons;
   c. first means for deriving a signal indicative of epithermal neutrons;
   d. second means for deriving a signal indicative of epithermal neutrons;
   e. means for taking the ratios of said thermal and said epithermal neutron signals respectively;
   f. means for generating signals indicative of the logarithms of said thermal and epithermal neutron ratios; and
   g. means for combining said logarithm signals to generate a signal representative of the macroscopic neutron absorption cross-section of the material.

18. An apparatus for quantitatively determining the macroscopic neutron absorption cross-section of a material, wherein said apparatus comprises:
   a. a neutron source for irradiating the material with neutrons;
   b. a pair of spaced detector means for monitoring radiation emanating from the material to generate a pair of signals indicative of thermal neutrons;
   c. a pair of spaced detector means for monitoring radiation emanating from the material to generate a pair of signals indicative of epithermal neutrons;
   d. means for determining a ratio signal for each respective pair of signals;

e. means for taking the logarithms of each of said ratio signals; and f. means for combining the logarithms of said ratio signals to generate a signal representative of the macroscopic neutron absorption cross-section of said material.

19. A method for monitoring fluid movements in a geological formation traversed by a well bore including the steps of:

a. logging the well bore to generate a first log trace representative of macroscopic neutron absorption cross-section;

b. relogging the well bore after the fluids in said geological formation have moved to generate a second log trace representative of macroscopic neutron absorption cross-section;

c. comparing said first and second log traces to derive an indication of the movement of fluid in said geological formation, either of said logging or relogging steps comprising the steps of:

(i.) passing a logging sonde through said borehole while continuously irradiating said formation with a source of neutrons;

(ii.) detecting an epithermal neutron flux with a first detector carried by said sonde and spaced from said source of neutrons;

(iii.) detecting a thermal neutron flux with a second detector carried by said sonde also spaced from said source of neutrons;

(iv.) generating electrical signals indicative of said detected epithermal neutron flux and of said thermal neutron flux respectively; and (v.) combining said electrical signals indicative of said detected epithermal neutron flux and of said thermal neutron flux to generate a log trace representative of the macroscopic neutron absorption cross-section of said geological formation according to the relationship:

$$SIGMA = A + B \log (FE) - C \log (FT)$$

where SIGMA is the macroscopic neutron absorption cross-section of said formation, (FE) is the signal indicative of epithermal neutrons, (FT) is the signal indicative of epithermal neutrons, (FT) is the signal indicative of thermal neutrons, and A, B, and C are constants.

20. A method for monitoring fluid movements in a geological formation traversed by a well bore including the steps of:

a. logging the well bore to generate a first log trace representative of macroscopic thermal neutron absorption cross-section;

b. relogging the well bore after the fluids in said geological formation have moved, to generate a second log trace representative of macroscopic thermal neutron absorption cross-section;

c. comparing said first and second logs to derive an indication of the movement of fluid in said geological formation, either of said logging or relogging steps comprising the steps of:

i. passing a logging sonde through said borehole while continuously irradiating said formation with a source of neutrons;

ii. detecting an epithermal neutron flux at each one of a first pair of detectors carried by said sonde and spaced different distances from said source of neutrons;

iii. detecting a thermal neutron flux at each one of a second pair of detectors carried by said sonde and spaced different distances from said source of neutrons;

iv. generating a first electrical signal indicative of the spatial distribution of epithermal neutrons;

v. generating a second electrical signal indicative of the spatial distribution of thermal neutrons;

vi. combining said first and second electrical signals to generate a signal representative of the macroscopic neutron absorption cross-section of said geological formation.

* * * * *